United States Patent
Yoshida et al.

(10) Patent No.: US 8,425,036 B2
(45) Date of Patent: Apr. 23, 2013

(54) OPTICAL TOMOGRAPHIC IMAGING APPARATUS AND CONTROL METHOD FOR THE SAME

(75) Inventors: Hirofumi Yoshida, Yokohama (JP); Norihiko Utsunomiya, Machida (JP)

(73) Assignee: Canon Kabushiki Kaisha, Tokyo (JP)

( * ) Notice: Subject to any disclaimer, the term of this patent is extended or adjusted under 35 U.S.C. 154(b) by 253 days.

(21) Appl. No.: 12/738,919

(22) PCT Filed: Mar. 16, 2010

(86) PCT No.: PCT/JP2010/054907
§ 371 (c)(1),
(2), (4) Date: Apr. 20, 2010

(87) PCT Pub. No.: WO2010/119750
PCT Pub. Date: Oct. 21, 2010

(65) Prior Publication Data
US 2011/0176107 A1 Jul. 21, 2011

(30) Foreign Application Priority Data
Apr. 13, 2009 (JP) ................................. 2009-097415

(51) Int. Cl.
*A61B 3/10* (2006.01)
*A61B 3/00* (2006.01)

(52) U.S. Cl.
USPC .......................................... 351/205; 351/246

(58) Field of Classification Search .................. 351/205, 351/246
See application file for complete search history.

(56) References Cited

U.S. PATENT DOCUMENTS

| 5,877,856 | A | 3/1999 | Fercher |
| 7,639,845 | B2 | 12/2009 | Utsunomiya |
| 2006/0114473 | A1 | 6/2006 | Tearney et al. |
| 2008/0117424 | A1* | 5/2008 | Teramura et al. ............. 356/450 |

(Continued)

FOREIGN PATENT DOCUMENTS

| EP | 1922990 A2 | 5/2008 |
| JP | 08-252256 A | 10/1996 |

(Continued)

OTHER PUBLICATIONS

Notification dated Oct. 27, 2011, forwarding an International Preliminary Report on Patentability dated Oct. 18, 2011, in International Application No. PCT/JP2010/054907.

International Search Report and Written Opinion of the International Searching Authority mailed Jul. 30, 2010, in counterpart International Application No. PCT/JP2010/054907.

*Primary Examiner* — Jordan Schwartz
(74) *Attorney, Agent, or Firm* — Fitzpatrick, Cella, Harper & Scinto (57) ABSTRACT

There is provided an optical tomographic imaging apparatus for imaging a tomographic image capable of setting characteristics of an optical system to accommodate to different positions on an object. The apparatus using an OCT system, includes: a scanning device for scanning measuring beams, an irradiating device for irradiating a different irradiation area on the object with the measuring beams scanned by the scanning device, an adjusting device for adjusting an irradiation position on the object of the measuring beams irradiated by the irradiating device, and a detecting device for detecting each combined beam produced from light interference between each of the return beams and the reference beams, characterized in that: the detecting device includes spectroscopy devices and a sensor, and a spectral width of the combined beam acquired with the sensor through the spectroscopy devices is set at a different spectral width by the spectroscopy devices.

17 Claims, 8 Drawing Sheets

U.S. PATENT DOCUMENTS

| | | |
|---|---|---|
| 2009/0091766 A1 | 4/2009 | Hirose |
| 2009/0285354 A1 | 11/2009 | Hirose et al. |
| 2010/0002241 A1 | 1/2010 | Hirose |
| 2010/0007894 A1 | 1/2010 | Suehira |
| 2010/0027019 A1 | 2/2010 | Suehira |
| 2010/0103374 A1 | 4/2010 | Hirose et al. |
| 2010/0182610 A1* | 7/2010 | Utsunomiya ............... 356/498 |
| 2010/0182612 A1 | 7/2010 | Yoshida et al. |
| 2011/0292395 A1* | 12/2011 | Fercher et al. ............... 356/451 |

FOREIGN PATENT DOCUMENTS

| | | |
|---|---|---|
| JP | 2875181 B2 | 3/1999 |
| WO | 2008-139799 A1 | 11/2008 |
| WO | 2008/148237 A1 | 12/2008 |
| WO | 2010-005091 A1 | 1/2010 |

* cited by examiner

☐ DETECTION BY FIRST LIGHT PATH

⬚ DETECTION BY SECOND LIGHT PATH

⬚ DETECTION BY THIRD LIGHT PATH

✕ DO NOT IRRADIATE

OPTICAL TOMOGRAPHIC IMAGING APPARATUS AND CONTROL METHOD FOR THE SAME

TECHNICAL FIELD

The present invention relates to an optical tomographic imaging apparatus and a control method for the same, and particularly to an optical tomographic imaging apparatus used for ophthalmologic diagnosis, and a control method for the same.

BACKGROUND ART

Adopting Optical Coherence Tomography (OCT) allows a tomographic image of an object (particularly, the fundus) to be imaged with a high resolution.

Particularly, OCT of the Fourier-domain system has a configuration capable of scanning at a time in the depth direction.

An optical tomographic imaging apparatus according to such Optical Coherence Tomography is hereinafter called "an OCT apparatus".

An OCT apparatus for ophthalmology may include an important measured position such as the macula and the optic disc. Conventionally, many apparatuses for diagnosing eye disease may measure these two positions with an OCT apparatus using a single beam.

For such conventional OCT apparatus for ophthalmology using a single beam, it has been desired to measure with a wide angle of view to cover both of the above mentioned macula and the optic disc. In these measurements, a measurement is made with a wide angle of view, and subsequently image information of the macula and the optic disc is acquired.

Japanese Patent No. 2875181 discloses an OCT apparatus that includes a plurality of light sources, an object light imaging optical system common to the plurality of light sources, and a plurality of optical sensors discretely disposed at positions corresponding to a common reference beam imaging light source system and the light sources.

The Publication describes that data is concurrently acquired at many points, and data at many points is acquired with a reference beam being made shifted, enabling for data acquisition at a high speed.

DISCLOSURE OF THE INVENTION

As described above, a measurement of a conventional OCT apparatus for ophthalmology using a single beam, is made with a wide angle of view to cover both of the macula and the optic disc.

Such a measurement with a wide angle of view takes much time to measure, resulting in a position shift or failure in an image caused by movement of the eye ball represented by an involuntary eye movement.

Japanese Patent No. 2875181 mentioned above discloses that the OCT apparatus having a plurality of light sources is used to acquire data at many points at a time, and thereby data can be acquired at a high speed, but it does not consider setting characteristics of an optical system to accommodate an imaged position when acquiring a tomographic image.

Particularly in a case when an object is the eye ball, setting characteristics of the optical system to accommodate these positions at imaging and acquiring a tomographic image of the macula and the optic disc on the fundus has not been considered at all.

An object of the present invention, in view of problems described above, is to provide an optical tomographic imaging apparatus capable of imaging a tomographic image of an object by irradiating different positions on the object with light including a plurality of measuring beams, and setting characteristics of an optical system to accommodate to these positions, and a control method for the same.

An optical tomographic imaging apparatus provided by the present invention is an optical tomographic imaging apparatus for imaging a tomographic image of an object by using combined beams produced from interference between reference beams and a plurality of return beams generated due to irradiation of the object with a plurality of measuring beams, including: a scanning device for scanning the plurality of measuring beams; an irradiating device for irradiating a different irradiation area on the object with the plurality of measuring beams scanned by the scanning device; an adjusting device for adjusting an irradiation position on the object of the plurality of measuring beams irradiated by the irradiating device; and a detecting device for detecting each combined beam produced from light interference between each of the plurality of return beams and the reference beams, characterized in that: the detecting device includes a plurality of spectroscopy devices and a sensor; and a spectral width of the combined beam acquired with the sensor through the plurality of spectroscopy devices is set at a different spectral width by the plurality of spectroscopy devices.

The present invention can realize an optical tomographic imaging apparatus capable of imaging a tomographic image of an object by irradiating a different position on the object with light including a plurality of measuring beams, and setting characteristics of an optical system to accommodate to these positions, and a control method for the same.

Further features of the present invention will become apparent from the following description of exemplary embodiments with reference to the attached drawings.

BEST MODES FOR CARRYING OUT THE INVENTION

Exemplary Embodiments

Now, exemplary embodiments of the present invention will be described hereinafter.

Embodiment 1

In a first exemplary embodiment, an optical tomographic imaging apparatus (OCT apparatus) to which the present invention is applied is described with reference to FIG. 1.

Figure 1:
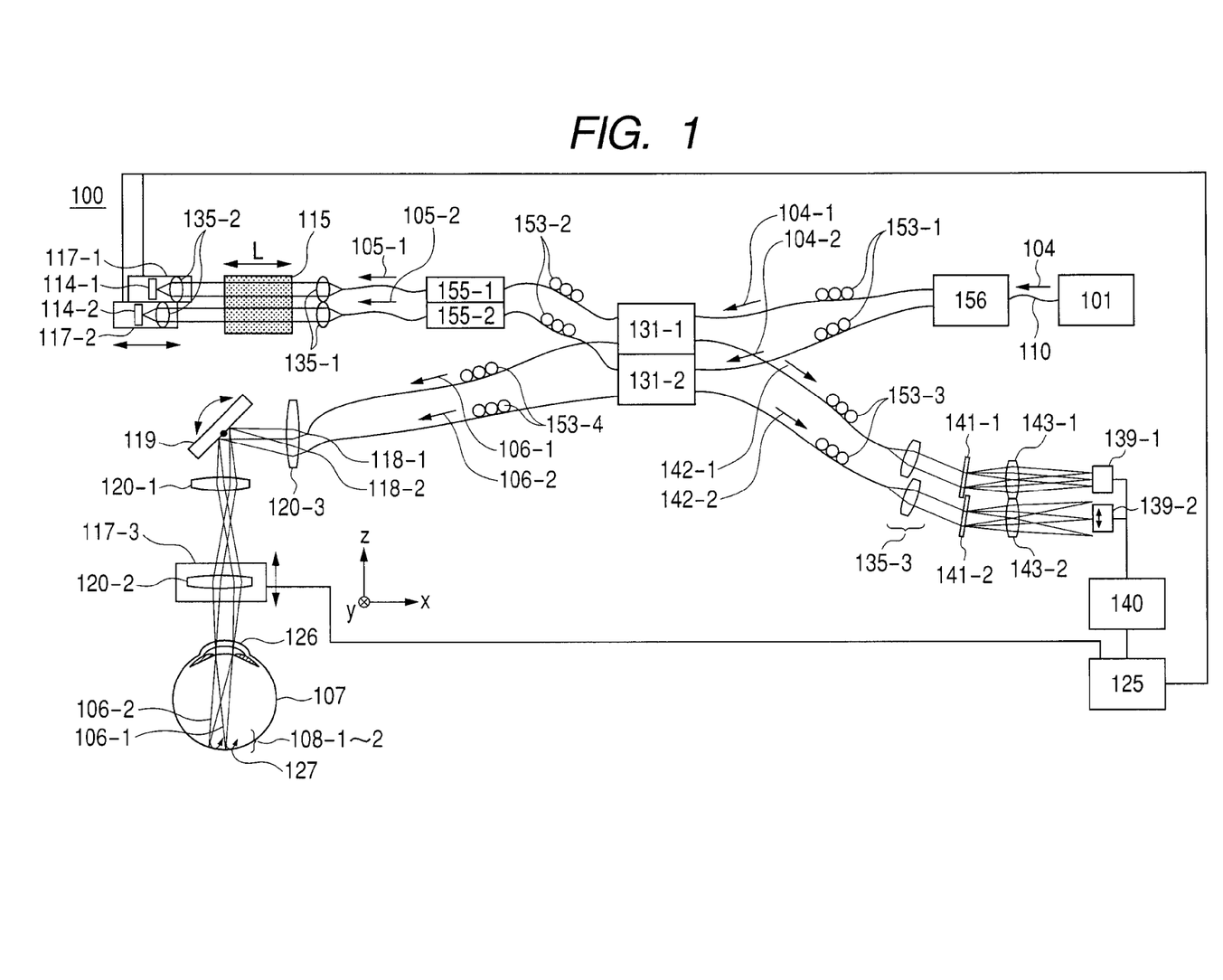
FIG. 1 illustrates a configuration of an optical tomographic imaging apparatus according to a first and second exemplary embodiment of the present invention.

An OCT apparatus 100 in the exemplary embodiment, as illustrated in FIG. 1, is a Michelson interferometer as a whole.

That is, light emitted from a light source is split into a measuring beam and a reference beam.

Then, a configuration includes an OCT system in which the measuring beam has a plurality of measurement light paths, and a return beam formed of a plurality of measuring beams and a reference beam through a reference light path are combined with each other for light interference to produce a plurality of combined beams, and by using the plurality of combined beams, a tomographic image of an object is imaged.

Specifically, as illustrated in FIG. 1, an emitted beam 104 emitted from a light source 101 is directed through a single-mode fiber 110 to enter an optical coupler 156, and split into an emitted beam 104-1 having a first light path of two light paths and an emitted beam 104-2 having a second light path by the optical coupler 156.

Further, each of the emitted beams 104-1 and 104-2 having these two light paths passes through a polarization controller 153-1, and is split into reference beams 105-1 and 105-2, and measuring beams 106-1 and 106-2 by optical couplers 131-1 and 131-2, respectively, with a intensity ratio of 50:50.

The measuring beam 106-1 (first measuring beam) and the measuring beam 106-2 (second measuring beam) split in such a way having the two light paths are reflected or scattered by the retina 127 etc. in an eye to be inspected 107, which is an object to be observed, to form return beams 108-1 and 108-2, respectively, which come back. That is, a plurality of return beams are generated corresponding to a plurality of irradiation beams. Then, the return beams 108-1 and 108-2 are combined with the reference beams 105-1 and 105-2 traveling through reference light paths by the optical couplers 131-1 and 131-2, respectively.

The reference beams 105-1 and 105-2, and the return beams 108-1 and 108-2 are combined with each other, respectively, producing combined beams 142-1 and 142-2, respectively. Subsequently, the combined beams 142-1 and 142-2 are separated into their wavelength components by transmission diffraction gratings 141-1 and 141-2, respectively, which enter line cameras (line sensors) 139-1 and 139-2 that function as a sensor.

The line cameras 139-1 and 139-2 convert light intensities into a voltage for each of positions (wavelengths), and by using the signal, a tomographic image of the eye to be inspected 107 is formed.

However, a device for branching into a plurality of light paths is not limited to this, but the optical coupler 156 may be disposed on the side of the object of the optical couplers 131-1 and 131-2 and on the side of a reference mirror to branch into two measuring beams and two reference beams, respectively. Alternatively, on the side of the reference mirror, the optical coupler 156 may not be disposed, and the reference beam may have only one light path.

Further, here, the case of using a plurality of line cameras (line sensors) has been described, but one line camera may be used.

Next, the vicinity of the light source 101 is described.

The light source 101 is a Super Luminescent Diode (SLD) which is a typical low-coherence light source. The light source has the wavelength of 830 nm and the bandwidth of 50 nm.

Here, the bandwidth affects resolution on a provided tomographic image in the optical axis direction, so that it is an important parameter.

Further, a type of light source selected here is the SLD, but the light source may be any types capable of emitting low-coherence light, and Amplified Spontaneous Emission (ASE) may be also used.

As the wavelength, near-infrared radiation is appropriate with consideration for measuring the eye. Further, the wavelength affects resolution on a provided tomographic image in the lateral direction, so that it is desirably as short as possible, and here the wavelength is 830 nm. Other wavelengths may be used depending on a measured position on an object to be observed.

Next, a light path of the reference beam 105 is described.

The reference beams 105-1 and 105-2 through the two light paths split by the optical couplers 131-1 and 131-2 pass through a polarization controller 153-2 and fiber length varying apparatuses 155-1 and 155-2, and are formed by a lens 135-1 to be approximately collimated beams having a diameter of 1 mm, which are emitted therefrom.

Next, the reference beams 105-1 and 105-2 pass through a dispersion compensation glass 115, and are focused on mirrors 114-1 and 114-2 by a lens 135-2.

Next, the reference beams 105-1 and 105-2 change their direction at the mirrors 114-1 and 114-2, and come back toward the optical couplers 131-1 and 131-2.

Next, the reference beams 105-1 and 105-2 pass through the optical couplers 131-1 and 131-2, and are directed to the line cameras 139-1 and 139-2.

Here, the dispersion compensation glass 115 compensates the reference beams 105 for dispersion produced when the measuring beams 106 go to and come back from the eye to be inspected 107.

Here, a representative value of an average diameter of Japanese eye balls is adopted for the value of L, as L=23 mm.

Electrically driven stages 117-1 and 117-2 can move in the directions shown by the arrows, and adjust and control the optical path length of the reference beams 105.

Also, the electrically driven stages 117-1 and 117-2 can be controlled by a computer 125 at a high speed.

The electrically driven stages 117-1 and 117-2 control positions of the lenses 135-2 and the mirrors 114, and allow for change in the optical path length of each of the reference beams 105-1 and 105-2 independently.

Further, the fiber length varying apparatuses 155-1 and 155-2 are installed for the purpose of finely adjusting the length of each of the fibers, and the optical path length of each of the reference beams 105-1 and 105-2 can be adjusted corresponding to a measured position of each of the measuring beams 106-1 and 106-2, and the apparatuses can be controlled by the computer 125.

Next, a light path of the measuring beam 106 is described.

The measuring beams 106-1 and 106-2 split by the optical couplers 131-1 and 131-2 pass through a polarization controller 153-4, and are formed by a lens 120-3 to be approximately collimated beams having a diameter of 1 mm, which are emitted therefrom, and enter a mirror of an XY scanner 119 constituting a scanning device.

Here, for the simplicity, the XY scanner 119 is shown as one mirror, but actually two mirrors, one for X scanning and the other for Y scanning, are disposed close to each other, and are used to scan the retina 127 in the direction perpendicular to the optical axis in the raster scan mode.

Further, lenses 120-1, 120-3 etc. are adjusted so that the center of each of the measuring beams 106-1 and 106-2 coincides with the rotation center of the mirror of the XY scanner 119.

The lens 120-1 and a lens 120-2 are an optical system for scanning the retina 127 with the measuring beams 106-1 and 106-2, respectively, and play a role in scanning the retina 127 with the measuring beams 106 using the vicinity of the cornea 126 as a pupil of the optical system.

The measuring beams 106-1 and 106-2 are adapted to form an image on the macula and the optic disc on the fundus, respectively, which are different desired irradiation areas.

Both beams form an angle therebetween, which is Δω=approximately 20°. Accordingly, fiber ends 118-1 and 118-2, and the lenses 120-1, 120-2 and 120-3 are adapted to provide the angle of approximately 20°.

The measuring beams 106-1 and 106-2 having the angle Δω therebetween form an image on the macula and the optic disc, respectively.

Because the angle Δω has an individual difference, the lenses 120-1, 120-2 and 120-3, and the fiber ends 118-1 and 118-2 can be adjusted to provide the proper angle for each individual.

Specifically, the lenses 120-1 and 120-3 are made of a plurality of lenses. Any of the plurality of lenses is moved in the optical axis direction so that a magnification is varied. Alternatively, there may be provided, between the fiber ends 118-1 and 118-2, and the cornea 126, a magnification varying mechanism (not shown) which includes a plurality of lenses similar to the above-mentioned ones and in which the plurality of lenses are moved in the optical axis direction, and thereby a magnification can be varied.

Also, an object point position changing device may be provided that can move positions of the fiber ends 118-1 and 118-2 in a plane perpendicular to the optical axis.

As described above, it is adapted so that an adjusting mechanism for adjusting irradiation positions of the measuring beams through the first and second light paths is provided, and the measuring beams 106-1 and 106-2 form an image on the macula and the optic disc on the fundus portion, respectively.

The XY scanner 119 is driven so that the center of each of scanning range coincides with the center of each of the macula and the optic disc having a displacement Dw therebetween, providing a scanned image through each of the measuring beams. For example, the XY scanner 119 is driven so that a range of ±5° can be scanned.

Also, an electrically-driven stage 117-3 can be moved in the directions shown by the arrow, and adjust and control the position of an associated lens 120-2. The position of the lens 120-2 is adjusted, so that the measuring beams 106 can be focused on a desired layer of the retina 127 in the eye to be inspected 107 to observe.

Further, it can be applied to the case where the eye to be inspected 107 has a refractive error. Once the measuring beams 106-1 and 106-2 enter the eye to be inspected 107, the measuring beams are reflected or scattered by the retina 127 to form the return beams 108-1 and 108-2, which pass through the optical coupler 131-1 and 131-2, and are directed to the line cameras 139.

Here, the electrically-driven stage 117-3 can be controlled by the computer 125 at a higher speed, compared to the magnification varying mechanism.

In the exemplary embodiment, the fiber ends 118-1 and 118-2 are adapted to be disposed on the same plane (XZ plane), but, not limited to this, they may be disposed in the direction perpendicular to the plane of FIG. 1 (Y direction), or adapted to have both components of the direction. A manner for adjusting the adjusting mechanism is similar to the above-mentioned.

Adopting the configuration described above allows for scanning the macula and the optic disc at a time, and a range for scanning is limited to the macula and the optic disc, and thereby an image necessary for diagnosis can be provided while a measuring time is largely reduced.

Next, a configuration of a measuring system (configuration of a spectroscopy device) in the OCT apparatus in the exemplary embodiment is described.

The return beams 108-1 and 108-2 formed from reflection or scattering by the retina 127 and respectively having the first and second light path, and the reference beams 105-1 and 105-2 are combined with each other by the optical couplers 131-1 and 131-2, respectively.

The combined beams 142-1 and 142-2 are emitted from the fiber ends, pass through the polarization controller 153-3, and are formed by lenses 135-3 to be approximately collimated beams.

The approximately collimated beams are irradiated to the transmission diffraction grating 141-1 (first spectroscopy device) and the transmission diffraction grating 141-2 (second spectroscopy device) that constitute a first detecting device and a second detecting device, respectively, and separated into their wavelength components, respectively.

The separated spectral beams are focused by focusing lenses 143-1 and 143-2, and light intensities are converted into a voltage for each of positions (wavelengths) by the line camera 139-1 (first camera) and the line camera 139-2 (second camera).

The line cameras 139-1 and 139-2 observe interference fringes in a spectral region in a wavelength axis.

Next, a spectroscopy portion is described more specifically.

An OCT apparatus has general, known characteristics that a wider spectral width has a higher resolution in OCT, and a higher wavelength resolution in spectroscopy has a wider measurable width in the depth direction.

These may be expressed by the following expressions 1 and 2:

$$R=1/(2\Delta K) \qquad \text{expression 1}$$

$$D=N/(2\Delta K) \qquad \text{expression 2}$$

Where, R is the resolution in OCT, ΔK is the wave number width acquired by the line camera, D is the measurable width in the depth direction in OCT, and N is the number of pixels of the line camera used for imaging.

However, the spectral width is a range of light wavelengths entering N pixels of the line camera, and is a difference $\lambda_{max}-\lambda_{min}$ between the maximal wavelength $\lambda_{max}$ and the minimal wavelength $\lambda_{min}$.

The wave number width ΔK may be expressed by $\Delta K=1/\lambda_{min}-1/\lambda_{max}$.

Also, the resolution in OCT is generally defined as a half of the coherence length.

From these factors, the larger ΔK is, the smaller R becomes (the higher resolution in OCT becomes), and let N be constant, then the smaller ΔK is (the higher the wavelength resolution in spectroscopy is), the larger D becomes (wider measurable width in the depth direction).

The term "wavelength resolution" used here is the wavelength width provided per pixel and is obtained by dividing the spectral width by the number of pixels of the line camera used for imaging.

However, an actual wavelength resolution, according to the definition here, generally becomes larger than the wavelength resolution because of optical aberration of lenses.

As illustrated in FIG. 1, in the case of a measurement using a plurality of measuring beams, it is desirable that a speed at which each of the plurality of measuring beams measures be equal, and, for the purpose, it is necessary that the line cameras used for imaging have the same number of pixels N.

In such a case, each of the combined beams through each of the light paths is set to have a different $\Delta K$, and thereby, the following two measurement methods can be performed:

(1) first measurement method: $\Delta K$ is large: measurement of a narrow range in the depth direction with a high resolution (2) second measurement method: $\Delta K$ is small: measurement of a wide range in the depth direction with a comparably low resolution.

The two measurement methods are used to measure the macula and the optic disc as described above, so that a measurement suited to their characteristics can be made, allowing for an efficient measurement.

Figure 2A:
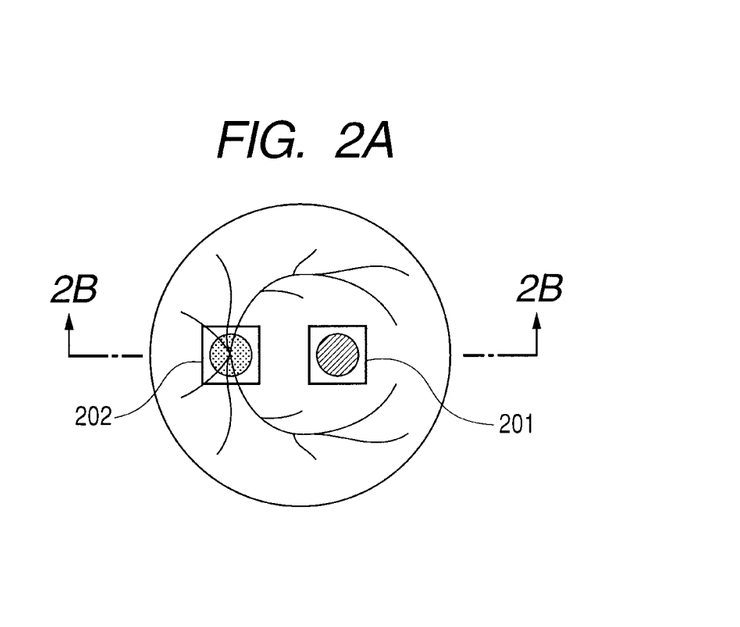
FIG. 2A and FIG. 2B are a schematic view and a cross-sectional view thereof for illustrating the macula and the optic disc on the fundus in the first exemplary embodiment of the present invention.
Figure 2B:
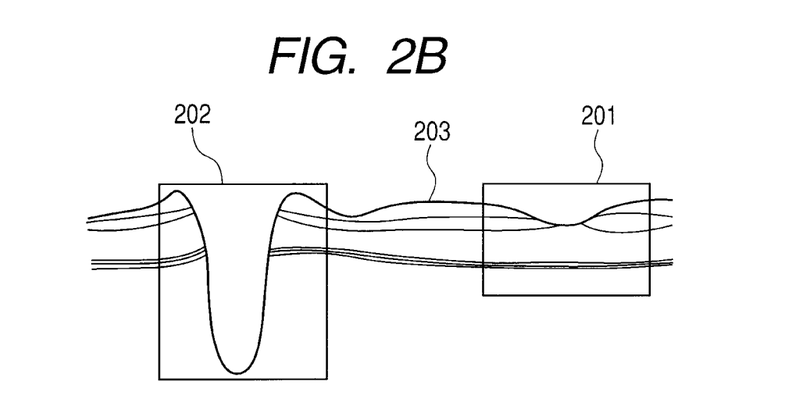

FIGS. 2A and 2B are schematic views for illustrating the macula 201 and the optic disc 202.

FIG. 2A illustrates a view seen from the optical axis in FIG. 1, and FIG. 2B illustrates a cross-sectional view thereof.

The optic disc 202 has the inner basement membrane 203 that dives down deep, compared to the macula 201, so that, for measuring it by OCT, it is necessary to measure a wide range.

Accordingly, one of the measurement methods described above, the first measurement method is applied to the macula 201 having a narrow range in the depth direction, and the other, the second measurement method is applied to the optic disc 202 having a wide range in the depth direction, and thereby, characteristics of the optical system can be configured to accommodate to a position.

A manner for performing the first and second measurement method by setting $\Delta K$ at a different state is described below.

Let the focal length of the focusing lenses 143-1 and 143-2 be f, let the width of the dispersion angle in which the wavelength width of the light source 101 is diffracted by the transmission diffraction gratings 141-1 and 141-2 be $\Delta\theta$, and let the spectral width of an image formed on the line cameras 139-1 and 139-2 be $\Delta y$, then the following expression 3 may hold:

$$\Delta y = f \tan(\Delta\theta) \quad \text{expression 3}$$

The term "dispersion angle" is the angle at which a monochromatic light beam is diffracted when it enters a diffraction grating.

Let $\Delta\theta$ be constant (the case where the transmission diffraction gratings 141-1 and 141-2 have the equal pitch), then focusing lenses 143-1 and 143-2 are set to have a different focal length, respectively, and thereby $\Delta y$ can be set at a different state.

$\Delta\theta$ is determined by the wavelength width of the light source and the pitch of the diffraction grating. The term "pitch" is the amount associated with the width of a pattern periodically carved in the diffraction grating, and the amount is shown by the number of patterns carved per mm (/mm).

Here, let the incidence angle on the diffraction grating be $\alpha$, let the diffraction angle be $\beta$, let the pitch be p, and let the wavelength be $\lambda$, then the following expression 4 may hold:

$$\sin \alpha + \sin \beta = p\lambda \quad \text{expression 4}$$

When a diffraction grating is used that has the maximal diffraction efficiency at $\alpha=\beta$, the relation between $\Delta\theta$, the wavelength width of the light source, and the pitch of the diffraction grating may be shown by the following expression 5:

$$\alpha = \beta = \sin^{-1}(p\lambda/2) \quad \text{expression 5}$$

When p=1200/mm, and $\lambda$=840 nm, then $\alpha=\beta=30.26°$.

At this time, the diffraction angle $\beta$, when $\lambda$=865 nm, is 32.27°, and the diffraction angle $\beta$, when $\lambda$=815 nm, is 28.29°. Therefore, $\Delta\theta=32.27°-28.29°=3.98°$.

FIGS. 3A, 3B, 3C and 3D are schematic views for illustrating a situation where an image is formed on a line camera when $\Delta y$ is set at a different state.

Figure 3A:
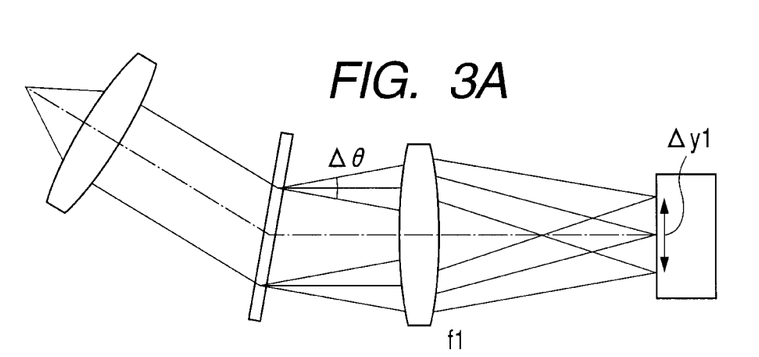
FIGS. 3A, 3B, 3C and 3D are schematic views for illustrating the case where a different spectral width is set in the first exemplary embodiment of the present invention.
Figure 3B:
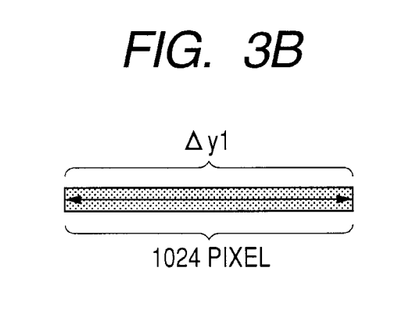
Figure 3C:
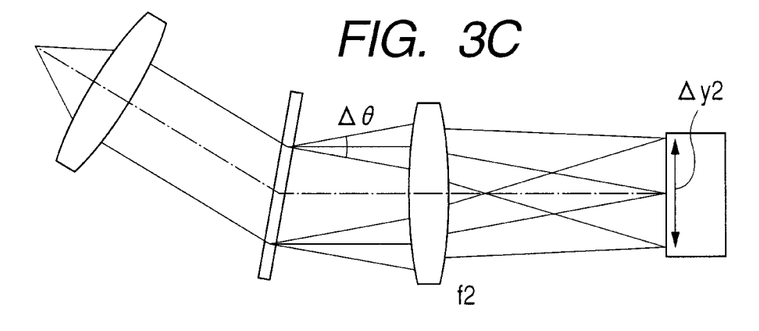
Figure 3D:
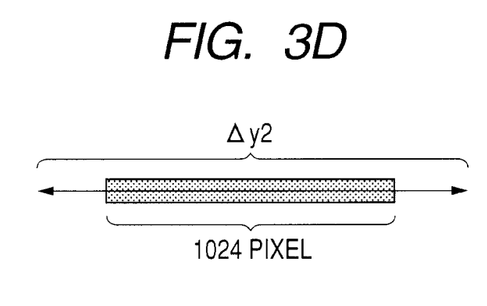

In FIGS. 3B and 3D, the arrow shows the spectral width on the line camera, and a colored portion is the line camera.

FIGS. 3A and 3B illustrate the case where the focal length is set short, and FIGS. 3C and 3D illustrate the case where the focal length is set long.

The focal length of the focusing lens shown in FIGS. 3A and 3B is designated by f1, and the focal length of the focusing lens shown in FIGS. 3C and 3D is designated by f2. Where, f1<f2.

The spectral width $\Delta y$ is changed into $\Delta y1$ or $\Delta y2$ due to a different focal length, and the wavelength width taken in by the line camera is varied, and thereby, $\Delta K$ in the expressions 1 and 2 can be changed.

For example, let f1 be 147 mm and let f2 be 200 mm, then $\Delta\theta$ takes 3.98°, which is substituted into the expression 3, providing $\Delta y1$=10.24 mm and $\Delta y2$=13.9 mm.

Let the pixel pitch of the line camera be 10 μm, and let the number of pixels N of the line camera used for imaging be 1024, then the length of $\Delta y$ which the line camera can take is 10.24 mm. That is, in the case of the focal length of f1=147 mm, the spectral width of 840±25 nm can be provided, but in the case of the focal length of f2=200 mm, only the spectral width of 840±18.4 nm can be provided. That is:

f1=147 mm: $\Delta K1=7.09\times10^{-2}$[1/μm]
R1=7.05 μm, D1=7.22 mm
f2=200 mm: $\Delta K2=5.22\times10^{-2}$[1/μm]
R2=9.58 μm, D2=9.81 mm Therefore, in the case where the focal length of the focusing lenses 143-1 and 143-2 is shortened, $\Delta K$ becomes large, and this case is applied to a measurement of the macula, and in the case where the focal length of the focusing lenses 143-1 and 143-2 is enlarged, $\Delta K$ becomes small, and this case is applied to a measurement of the optic disc, and thereby, characteristics of the optical system can be configured to accommodate to a position.

In such a manner, according to the configuration in the exemplary embodiment, light including a plurality of measuring beams is irradiated to a different position on an object, and characteristics of an optical system are set to accommodate to a position at acquiring a tomographic image, allowing for imaging efficiently.

Particularly, when the object is the eye ball, characteristics of the optical system are set to accommodate to the position at acquiring a tomographic image of the macula and the optic disc on the fundus portion, allowing for imaging efficiently.

Further, when the eye to be inspected is changed side to side, the macula and the optic disc become reversed, and responsive to this change, the optical system has to be changed.

Here, the focal lengths of the focusing lenses 143-1 and 143-2 are replaced with each other.

A method for replacing is that the focusing lenses 143-1 and 143-2 may be zoom lenses to vary the focal lengths, or the focusing lenses 143-1 and 143-2 may be replaced with each other.

Those focal length varying mechanisms may be used to respond to the case where the eye to be inspected is changed side to side. Alternatively, the fiber ends 118-1 and 118-2 may be replaced with each other.

A group of voltage signals converted from light intensities in the line cameras 139-1 and 139-2 are converted into digital values by a frame grabber 140, which are data processed by the computer 125 to form a tomographic image.

Here, the line cameras 139-1 and 139-2 have 1024 pixels, respectively, and intensity of the combined beams 142-1 and 142-2 can be provided for each of wavelengths.

In the above-mentioned, to set a measuring speed at an equal level, the number of pixels N of 1024 is used to image both of images of the macula and the optic disc, but the number of pixels N used for imaging each of the images may be varied, respectively. For example, let the focal lengths of the focusing lenses 143-1 and 143-2 be an equal focal length of f1=147 mm, then $\Delta y$=10.24 mm.

Let the pixel pitch of the line cameras be 10 μm, let the number of pixels N of one of the line cameras used for imaging be N1=1024, and let the other be N2=512, then the lengths of $\Delta y$ that the line cameras can take are 10.24 mm and 5.12 mm, respectively.

That is, when 1024 pixels are used for imaging, the spectral width of 840±25 nm can be provided, but when 512 pixels are used for imaging, only the spectral width of 840±12.5 nm can be provided. That is:

N1=1024 pixels: $\Delta K1$=7.09×10$^{-2}$[1/μm]
R1=7.05 μm, D1=7.22 mm
N2=512 pixels: $\Delta K2$=7.09×10$^{-2}$[1/μm]
R2=14.1 μm, D2=7.22 mm In this case, the measurable widths in the depth direction are equal, but the resolution in OCT becomes higher in the case of N1=1024 pixels. On the other hand, the measurement speed becomes lower in the case of N1=1024 pixels. Therefore, according to this measurement method, measured positions can be divided into a position measured with a higher resolution and a longer time, and a position measured with a lower resolution and a shorter time, and characteristics of the optical system are set to accommodate to these positions, allowing for imaging efficiently.

The conversion from light intensities to voltages and the data processing are as described above.

That is, in the optical tomographic imaging apparatus of the present invention, a plurality of spectroscopy devices (a plurality of units including a diffraction grating and a lens) can set at least one of spectral widths of the combined beams that the line cameras (sensors) take, at a different spectral width.

Next, acquisition of a tomographic image using an OCT apparatus is described.

Here, with reference to FIGS. 4A to 4D, acquisition of a tomographic image of the retina 127 (plane parallel to the optical axis) is described.

Figure 4A:
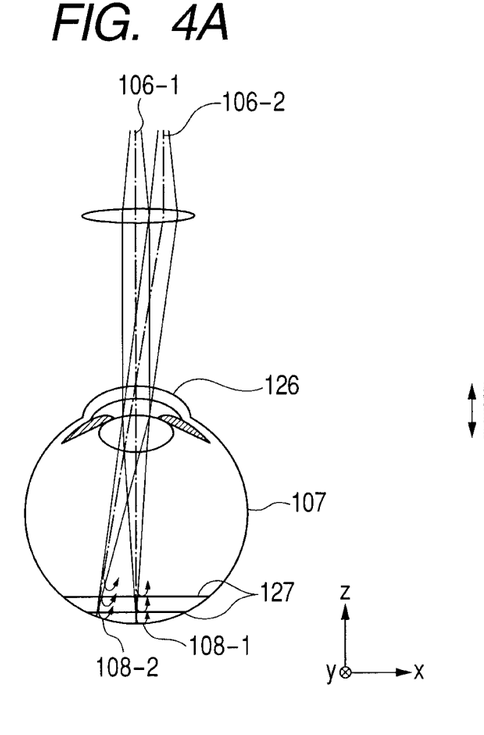
FIGS. 4A, 4B, 4C and 4D illustrate acquisition of a tomographic image by the OCT apparatus in the first exemplary embodiment of the present invention.

FIG. 4A illustrates a situation in which the eye to be inspected 107 is observed by an OCT apparatus 100.

A like or corresponding component as that shown in FIG. 1 is designated by a like symbol, and description of a redundant component is omitted.

As illustrated in FIG. 4A, once the measuring beams 106-1 and 106-2 enter the retina 127 through the cornea 126, they are reflected or scattered at various positions to form the return beams 108-1 and 108-2, which arrive at the line cameras 139-1 and 139-2 with a delay time caused at each of the positions.

In this embodiment, the light source 101 has a wide bandwidth and a short spatial coherence length. Hence if the optical path length of the reference light path is approximately equal to the optical path length of the measurement light path, then the line cameras 139-1 and 139-2 can detect interference fringes.

As described above, what the line cameras 139-1 and 139-2 acquire are interference fringes in a wavelength axis in a spectral region.

Next, the interference fringes, which are information in the wavelength axis, are converted into interference fringes in a light frequency axis for each of the combined beams 142-1 and 142-2, with consideration for characteristics of the line cameras 139-1 and 139-2 and the transmission diffraction gratings 141-1 and 141-2.

Further, the converted interference fringes in the light frequency axis are inverse Fourier transformed, and thereby information in the depth direction can be provided.

Figure 4B:
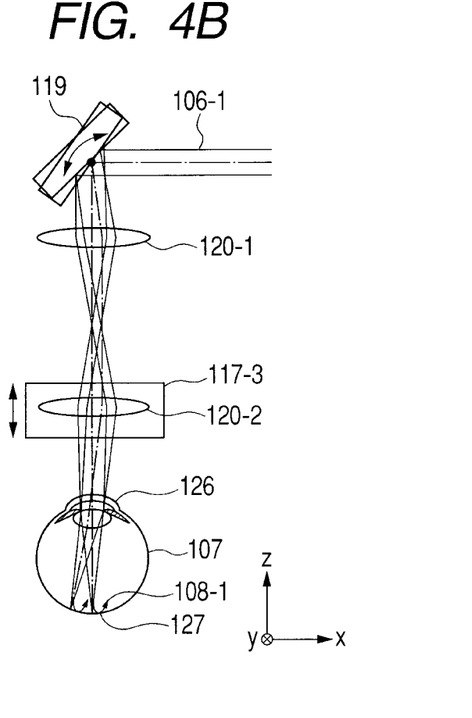

Further, as shown in FIG. 4B illustrating only the measuring beam 106-1 of the measuring beams for the simplicity, by detecting interference fringes while driving the X axis of the XY scanner 119, the interference fringes can be provided for each of positions in the X axis. That is, information in the depth direction can be provided for each of positions in the X axis.

Figure 4C:
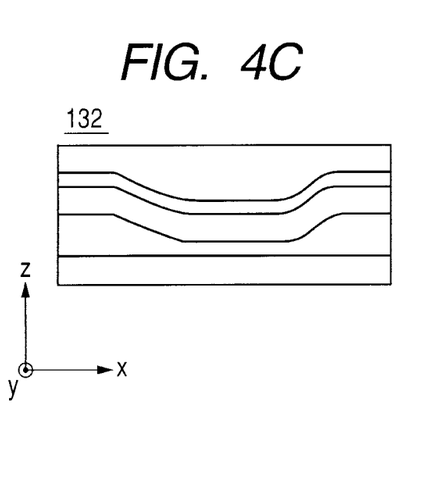

As the result, a two-dimensional distribution of the intensity of the return beam 108-1 in the XZ plane can be provided, which is namely a tomographic image 132 shown in FIG. 4C.

The tomographic image 132, as described above, is originally an array in which intensities of the return beam 108 are arranged, and displayed, for example, in gray scale display of the intensities.

Here, only the boundaries of a provided tomographic image are displayed to emphasize.

Figure 4D:
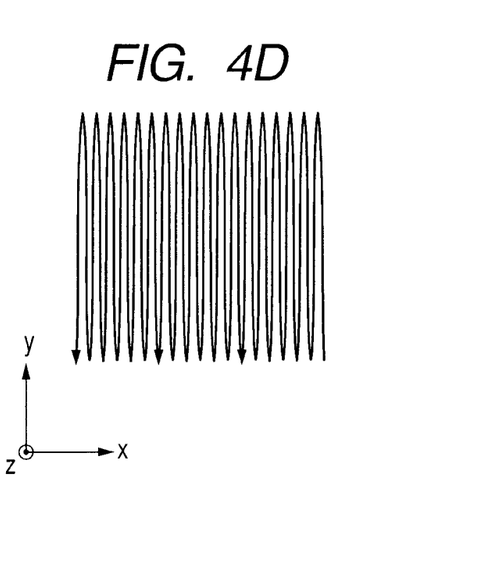

Also, as illustrated in FIG. 4D, the XY scanner 119 is controlled to scan the macula and the optic disc with the measuring beams 106-1 and 106-2, respectively, in the raster scan mode, and thereby, two tomographic images of the macula and the optic disc can be provided at a time and continuously.

Here, the scanning case where a main scanning direction of the XY scanner is the X axis direction, and a secondary scanning direction is the Y axis direction is shown, and as the result, a plurality of tomographic images in the YZ plane can be provided.

Embodiment 2

In the first exemplary embodiment, the focal length of the focusing lenses 143-1 and 143-2 is varied to measure the right and left eye. On the contrary, a second exemplary embodiment describes an example of a configuration in which a grating pitch of the transmission diffraction gratings 141-1 and 141-2 is varied.

The term "pitch" is the amount associated with the width of a pattern periodically carved in a diffraction grating, and shown by the number of patterns carved per mm (/mm).

An OCT apparatus 100 is arranged similar to the first exemplary embodiment, and description thereof is omitted.

FIGS. 5A, 5B, 5C and 5D illustrate schematic views for illustrating imaging by a line camera in which $\Delta y$ is set at a different state.

Figure 5A:
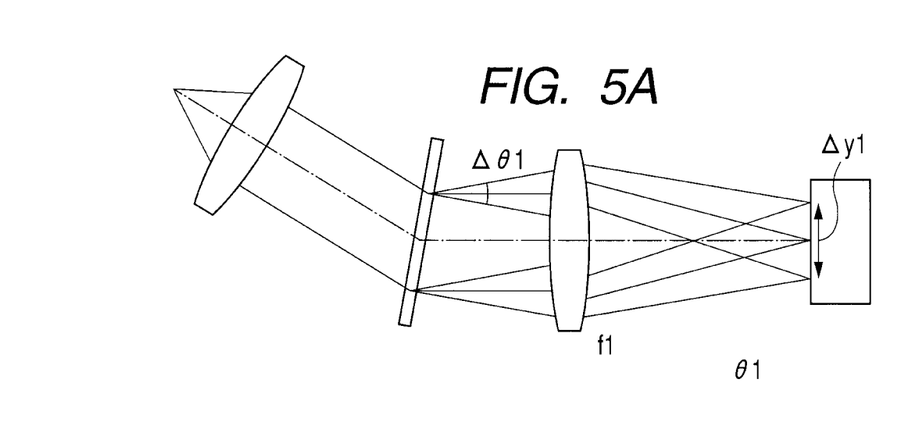
FIGS. 5A, 5B, 5C and 5D illustrate an example of a configuration for forming a different spectral width by setting a transmission diffraction grating at a different pitch in the second exemplary embodiment of the present invention.
Figure 5B:
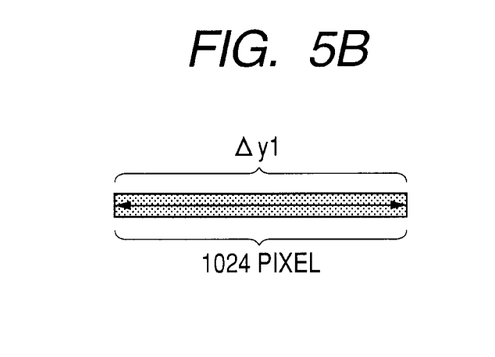
Figure 5C:
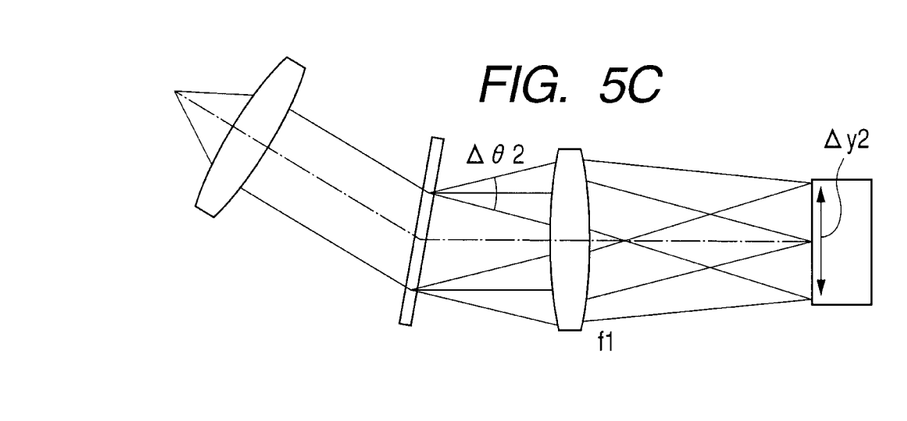
Figure 5D:
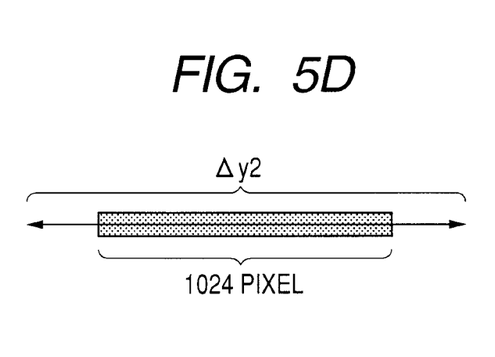

The arrows in FIGS. 5B and 5D show the spectral width on the line camera, and colored portions are the line cameras.

Also, FIGS. 5A and 5B illustrate the case where the transmission diffraction gratings 141-1 and 141-2 have a wide pitch, and FIGS. 5C and 5D illustrate the case where the transmission diffraction gratings 141-1 and 141-2 have a narrow pitch.

The pitch of the transmission diffraction gratings shown in FIGS. 5A and 5B is p1, and at this time, the width of the dispersion angle at which light is diffracted is $\Delta\theta 1$, and the pitch of the transmission diffraction gratings shown in FIGS. 5C and 5D is p2, and at this time, the width of the dispersion angle at which light is diffracted is $\Delta\theta 2$. Where, $\Delta\theta 1 < \Delta\theta 2$.

When the transmission diffraction gratings 141-1 and 141-2 have a wide pitch, the width of the dispersion angle $\Delta\theta$ at which light is diffracted becomes smaller, and on the contrary, when the pitch is narrow, $\Delta\theta$ becomes larger.

Accordingly, $\Delta y$ shown by the expression 3, in the former case, becomes smaller, and in the other case, $\Delta y$ becomes larger.

That is, there can be provided an equivalent effect as that when the focal length of the focusing lens is varied in the first exemplary embodiment.

Let the focal length f1 be 147 mm similar to the first exemplary embodiment, let p1 be 1200/mm, and let p2 be 1500/mm, then, using the expressions 3-5 similar to the first exemplary embodiment, the spectral width of 840±25 nm can be provided when the pitch is p1=1200/mm.

However, only the spectral width of 840±18.0 nm can be provided when the pitch is p2=1500/mm. That is:

p1=1200/mm: $\Delta K1 = 7.09 \times 10^{-2} [1/\mu m]$

R1=7.05 μm, D1=7.22 mm p2=1500/mm: $\Delta K2 = 5.10 \times 10^{-2} [1/\mu m]$

R2=9.81 μm, D2=10.0 mm

The width $\Delta y$ is changed into $\Delta y1$ or $\Delta y2$, which changes the wavelength width which the line camera takes, and thereby, $\Delta K$ in the expressions 1 and 2 can be varied.

In FIG. 5, FIGS. 5A and 5B illustrate the case of a large $\Delta K$, and FIGS. 5C and 5D illustrate the case of a small $\Delta K$.

Therefore, if the transmission diffraction gratings 141-1 and 141-2 have a wide pitch, $\Delta K$ becomes large, so that this case is applied to a measurement of the macula, and if the transmission diffraction gratings 141-1 and 141-2 have a narrow pitch, $\Delta K$ becomes small, so that this case is applied to a measurement of the optic disc, and thereby, characteristics of the optical system can be configured to accommodate to a position, allowing for imaging efficiently.

Embodiment 3

In the first exemplary embodiment, the optical system is changed responsive to changing the eye side to side. On the contrary, a third exemplary embodiment describes an example of a configuration in which an optical system for replacement is provided in advance.

Figure 6:
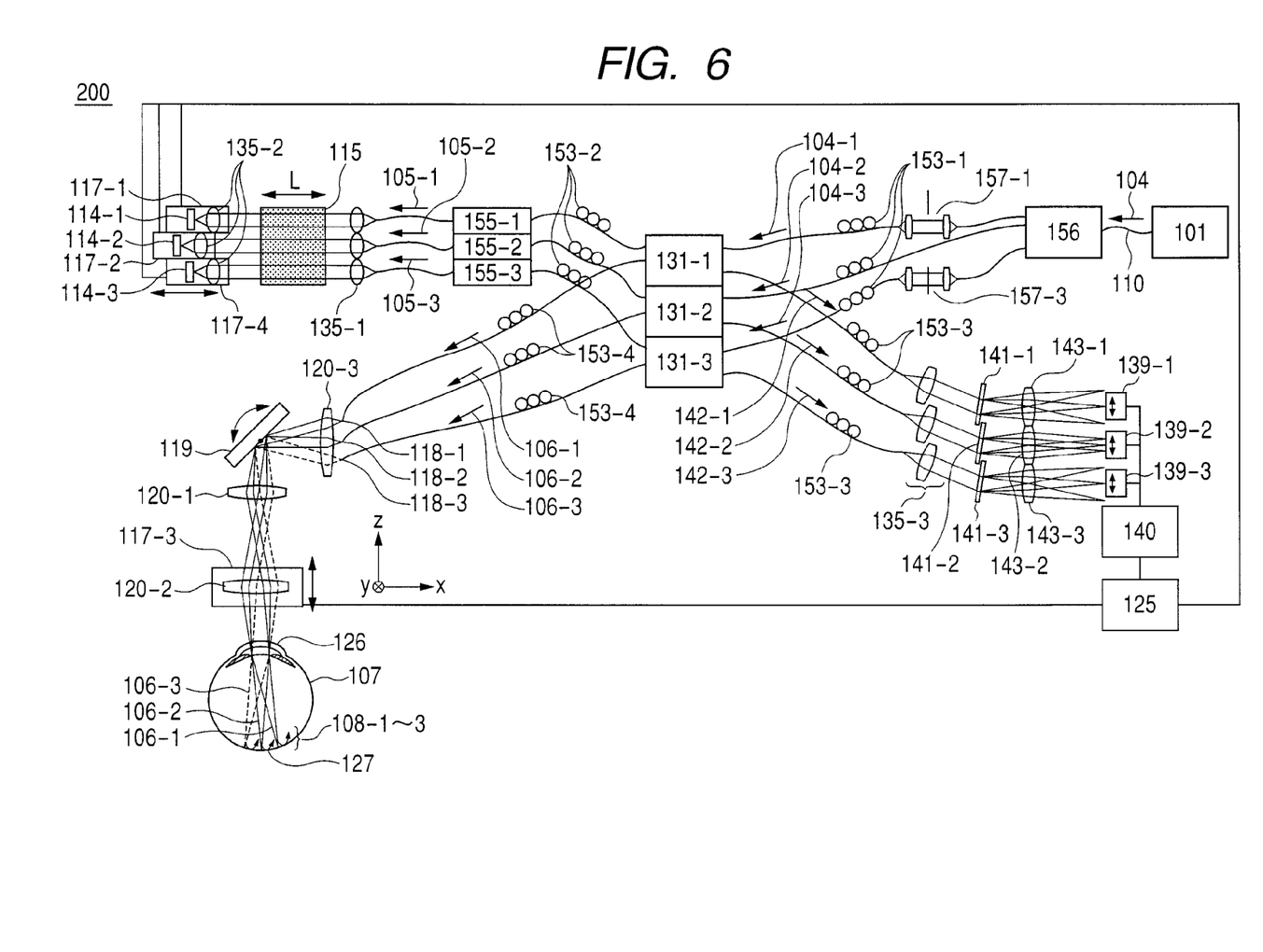
FIG. 6 illustrates a configuration of an optical tomographic imaging apparatus according to a third exemplary embodiment of the present invention.

That is, in the third exemplary embodiment, an OCT apparatus includes 3 light paths having a third light path, in addition to the first light path and the second light path, for directing 3 light path light beams (the first and second measuring beam, and a third measuring beam), and each of the light paths is configured as follows:

the first light path: for the optic disc (left eye)
the second light path: for the macula (left eye and right eye)
the third light path: for the optic disc (right eye).

FIG. 6 illustrates a configuration of a measuring system in the exemplary embodiment. This measuring system differs in that each of the components is added corresponding to the increase in the number of the light paths from 2 to 3, compared to the configuration of the measuring system in FIG. 1.

An OCT apparatus is designated by 200. A light source portion and a reference light path are changed only in configuration in which the two light paths in FIG. 1 is changed into the three light paths, and a duplicate description is omitted.

Next, a configuration for measuring the left eye in the measuring system of the exemplary embodiment is described.

Also the measuring system, basically, has a configuration in which 2 measuring beams are changed into 3 measuring beams, compared to the configuration of the measuring system in FIG. 1.

An emitted beam 104 emitted from a light source 101 is split into emitted beams 104-1, 104-2 and 104-3 by an optical coupler 156, and the emitted beams enter optical couplers 131-1, 131-2 and 131-3, respectively. Measuring beams 106-1, 106-2 and 106-3 split by optical couplers 131-1, 131-2 and 131-3 pass through polarization controllers 153-4 and are formed by a lens 120-3 to be approximately collimated beams having a diameter of 1 mm, respectively, which are emitted therefrom, and enter a mirror of an XY scanner 119.

Lenses 120-1 and 120-2 is an optical system for scanning the retina 127 with the measuring beams 106-1, 106-2 and 106-3, and play a role in scanning the retina 127 using the vicinity of the cornea 126 as a pupil of the optical system.

When the left eye is measured in a manner of this exemplary embodiment, it is adapted so that the measuring beam 106-1 forms an image on the optic disc, and the measuring beam 106-2 forms an image on the macula. The measuring beam 106-3 does not irradiate light at measuring the left eye.

On the one hand, when the right eye is measured, it is adapted so that the measuring beam 106-1 does not irradiate light, the measuring beam 106-2 forms an image on the macula, and the measuring beam 106-3 forms an image on the optic disc.

For the purpose, fiber ends 118-1, 118-2 and 118-3, and the lenses 120-1, 120-2 and 120-3 are adapted so that both of an angle between the measuring beams 106-1 and 106-2, and an angle between the measuring beams 106-2 and 106-3 are set at 20°, which is an angle between the macula and the optic disc.

The measuring beam 106-2 is used for measuring any of the left eye and the right eye, but the measuring beams 106-1 and 106-3 are replaced with each other according to a measurement of the left eye or the right eye. This switching is performed by shutters 157-1 and 157-3 in the light source portion.

FIGS. 7A, 7B, 7C and 7D illustrate configurations when the left eye is measured and when the right eye is measured.

Figure 7A:
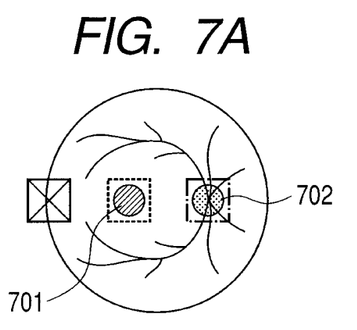
FIGS. 7A, 7B, 7C and 7D illustrate an irradiation pattern on the fundus in the third exemplary embodiment of the present invention.
Figure 7B:
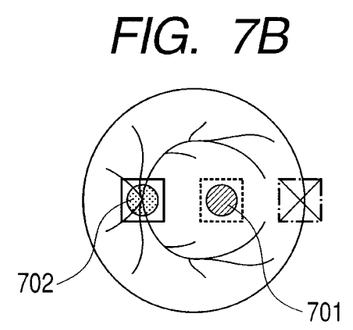

FIGS. 7A and 7B illustrate configurations of the exemplary embodiment. FIG. 7A illustrates a situation where the right eye is measured, and FIG. 7B illustrates a situation where the left eye is measured. Because positions of the macula and the optic disc become reversed in the right eye and the left eye, the three measurement light paths are provided in advance as described above. As illustrated in FIG. 7A, the optic disc 702 and the macula 701 in the right eye are measured using the third light path and the second light path, respectively. As illustrated in FIG. 7B, the optic disc 702 and the macula 701 in the left eye are measured using the first light path and the second light path, respectively.

The third light path is not used at measuring the left eye, and the first light path is not used at measuring the right eye.

Figure 7C:
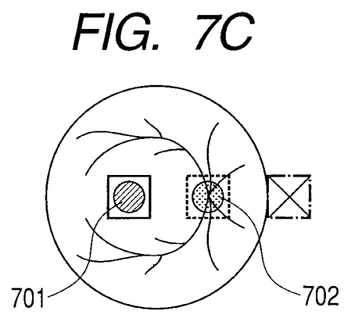
Figure 7D:
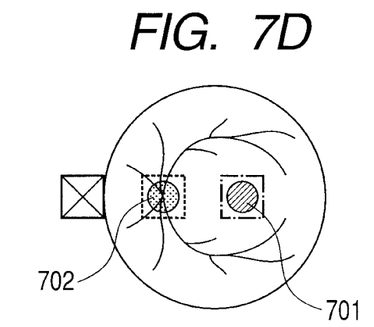

Further, FIGS. 7C and 7D also illustrate opposite configurations. In these configurations, as illustrated in FIG. 7C, the optic disc 702 and the macula 701 in the right eye are measured using the second light path and the first light path, respectively. As illustrated in FIG. 7D, the optic disc 702 and the macula 701 in the left eye are measured using the second light path and the third light path, respectively. That is, it is adapted so that:

the first light path: for the macula (right eye)
the second light path: for the optic disc (left eye and right eye)
the third light path: for the macula (left eye).

The first light path is not used at measuring the left eye, and the third light path is not used at measuring the right eye. These configurations are also allowed for a measurement.

A scan range and an adjusting device are similar to the first exemplary embodiment, and description thereof is omitted.

Note that, in this exemplary embodiment, a lens 114-3 for changing the direction of a reference beam 105-3 and an electrically-driven stage 117-4 for adjusting and controlling the optical path length of the reference beam 105-3 are installed in the reference light path.

Next, a configuration of a measuring system in the OCT apparatus of the exemplary embodiment (configuration of a spectroscopy device) is described.

The return beams 108-1, 108-2 and 108-3 which are beams reflected or scattered by the retina 127, and the reference beams 105-1, 105-2 and 105-3 are combined with each other by the optical couplers 131-1, 131-2 and 131-3, respectively.

Then, the combined beams 142-1, 142-2 and 142-3 are emitted from the fiber ends, and formed by lenses 135-3 to be approximately collimated beams.

These approximately collimated beams are irradiated to transmission diffraction gratings 141-1, 141-2 and 141-3, and separated into their wavelength components, respectively.

The separated spectral beams are focused by focusing lenses 143-1, 143-2 and 143-3, light intensities of which are converted into a voltage for each of positions (wavelengths) by line cameras 139-1, 139-2 and 139-3, respectively. The line cameras 139-1, 139-2 and 139-3 will observe interference fringes in a spectral region in a wavelength axis.

Next, a spectroscopy portion is described more specifically.

A measurement of the macula and the optic disc, as described regarding the configuration of the measurement light paths, is made by causing the beams to enter spectroscopes having a different $\Delta K$, respectively.

Similar to the first exemplary embodiment, a first measurement method is applied to a measurement of the macula and a second measurement method is applied to a measurement of the optic disc, as described below:

(1) first measurement method—$\Delta K$ is large: measurement of a narrow range in the depth direction with a high resolution (2) second measurement method—$\Delta K$ is small: measurement of a wide range in the depth direction with a comparably low resolution.

A method for varying $\Delta K$ is that, similar to the first exemplary embodiment, the focal lengths of the focusing lenses 143-1, 143-2 and 143-3 are set at a focal length different from each other, and thereby, $\Delta y$ is changed into $\Delta y1$ or $\Delta y2$.

Alternatively, similar to the second exemplary embodiment, the pitches of the transmission diffraction gratings 141-1, 141-2 and 141-3 may be changed. An example of a specific apparatus configuration is similar to the first or second exemplary embodiment, description thereof here is omitted.

FIGS. 8A, 8B, 8C, 8D, 8E and 8F illustrate a configuration of a spectroscopy device in the exemplary embodiment.

Figure 8A:
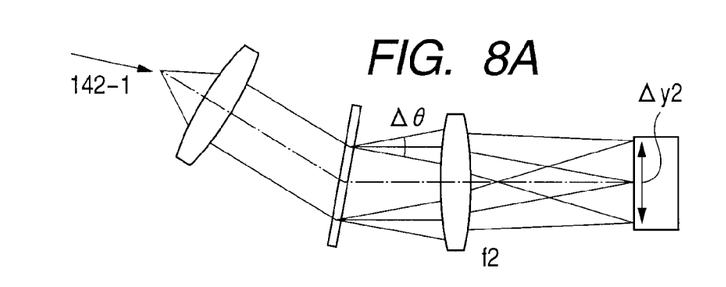
FIGS. 8A, 8B, 8C, 8D, 8E and 8F illustrate a spectroscopy device in the third exemplary embodiment of the present invention.
Figure 8B:
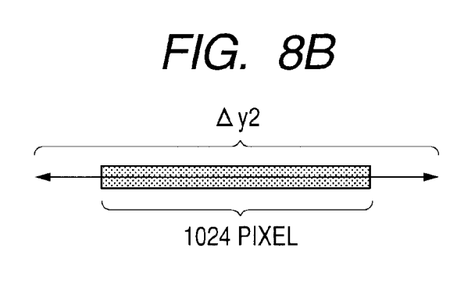
Figure 8C:
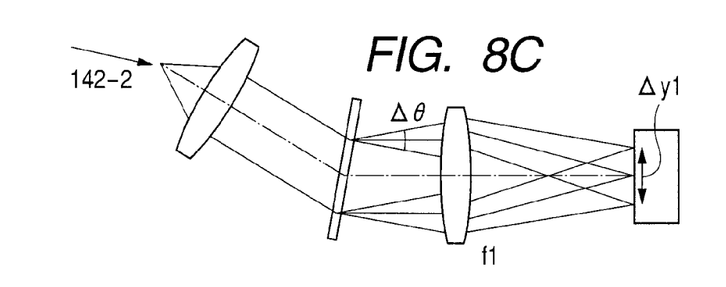
Figure 8D:
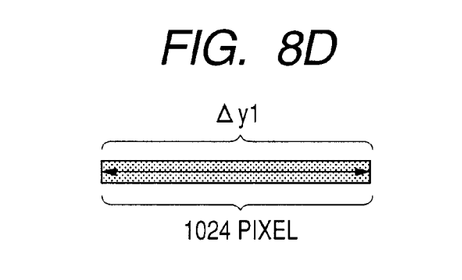
Figure 8E:
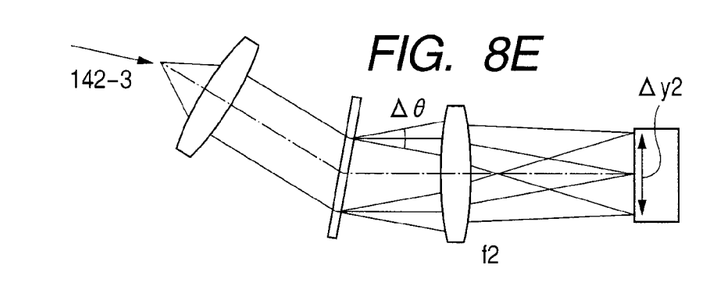
Figure 8F:
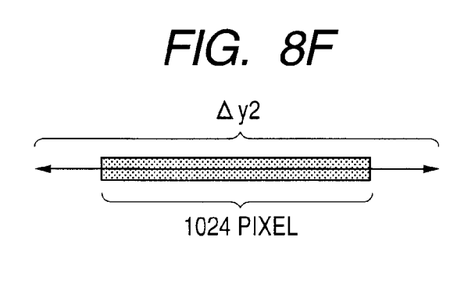

FIGS. 8A and 8B illustrate a spectroscopy device for measuring the optic disc (for the left eye), and FIGS. 8C and 8D illustrate a spectroscopy device for measuring the macula (for the left and right eye), and FIGS. 8E and 8F illustrate a spectroscopy device for measuring the optic disc (for the right eye). These spectroscopy devices separate the beams through the light paths 142-1, 142-2 and 142-3, respectively.

Two light paths in total are provided for measuring the optic disc, and in the two light paths (142-1 and 142-3), $\Delta y$ is enlarged to $\Delta y2$ by lengthening the focal length of the focusing lenses (or narrowing the pitch of the transmission diffraction gratings), and thereby, $\Delta K$ is reduced.

Further, at measuring the macula, $\Delta y$ is reduced to $\Delta y1$ by shortening the focal length of the focusing lens 143-2 in the light path 142-2 (or widening the pitch of the transmission diffraction gratings), and thereby, $\Delta K$ is increased. The spectroscopy devices are configured as described above, and a measurement of the macula and the optic disc is made.

In the configuration described above, the light path 142-1 for measuring the optic disc and the light path 142-2 for measuring the macula are used to measure the left eye, and the light path 142-3 for measuring the optic disc and the light path 142-2 for measuring the macula are used to measure the right eye.

Adopting the configuration as described above allows for a measurement without change in the focal lengths of the focusing lenses 143-1, 143-2 and 143-3, or replacement of the fiber ends 118.

A group of voltage signals converted from light intensities in the line cameras 139-1, 139-2 and 139-3 are converted into digital values by a frame grabber 140, which are data processed by the computer 125, forming a tomographic image.

Here, each of the line cameras 139-1, 139-2 and 139-3 have 1024 pixels, and can provide intensities of the combined beams 142-1, 142-2 and 142-3 for each of wavelengths. When the configurations illustrated in FIGS. 7C and 7D are adopted, two light paths in total are provided to measure the macula. In the two light paths (142-1 and 142-3), $\Delta y$ is reduced to $\Delta y1$ by shortening the focal lengths of the focusing lenses 143-1 and 143-3 (or widening the pitches of the transmission diffraction gratings 141-1 and 141-3), and thereby, $\Delta K$ is increased.

Also, at measuring the optic disc, $\Delta y$ is enlarged to $\Delta y2$ by lengthening the focal length of the focusing lens 143-2 in the light path 142-2 (or narrowing the pitch of the transmission diffraction grating 141-2), and thereby, $\Delta K$ is reduced. This allows for a measurement. Acquisition of a tomographic image is similar to the first exemplary embodiment, and description thereof is omitted.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2009-097415, filed Apr. 13, 2009, which is hereby incorporated by reference herein in its entirety.

The invention claimed is:

1. An optical tomographic imaging apparatus for acquiring at least a tomographic image of an object by using a plurality of combined beams produced from interference between reference beams and a plurality of return beams generated due to irradiation of the object with a plurality of measuring beams, the optical tomographic imaging apparatus comprising:

a scanning unit configured to scan the plurality of measuring beams;

an irradiating unit configured to irradiate different irradiation areas on the object, each area being located on the same surface intersecting with an optical axis of the plurality of measuring beams, with the plurality of measuring beams scanned by the scanning unit; and a detecting unit configured to detect each of the plurality of combined beams within a different measurable range in a depth direction of the object.

2. The optical tomographic imaging apparatus according to claim 1, wherein the detecting unit comprises: (a) a plurality of spectroscopy units, and (b) a plurality of sensors corresponding to the plurality of spectroscopy units, and wherein spectral widths of the plurality of combined beams acquired with the plurality of sensors through the plurality of spectroscopy units are set at different spectral widths by the plurality of spectroscopy units.

3. The optical tomographic imaging apparatus according to claim 1, further comprising a plurality of spectroscopy units, wherein the plurality of spectroscopy units include respective focusing lenses with each focusing lens having a different focal length, and respective diffraction gratings with each diffraction grating having a different pitch.

4. The optical tomographic imaging apparatus according to claim 3, wherein the focal length of each focusing lens is adapted to be variable.

5. The optical tomographic imaging apparatus according to claim 1, further comprising:

an adjusting unit configured to adjust an irradiation position of the plurality of measuring beams, wherein the adjusting unit includes one of a magnification varying unit and an object point position changing unit.

6. The optical tomographic imaging apparatus according to claim 1, wherein the object is an eyeball, wherein the plurality of measuring beams include a first measuring beam and a second measuring beam, wherein a combined beam produced from the first measuring beam is used to acquire a tomographic image of a macula on a fundus portion in the eyeball, and wherein a combined beam produced from the second measuring beam is used to acquire a tomographic image of an optic disc on the fundus portion in the eyeball.

7. An optical tomographic imaging method for acquiring at least a tomographic image of an object by using a plurality of combined beams produced from interference between reference beams and a plurality of return beams generated due to irradiation of the object with a plurality of measuring beams, the optical tomographic imaging method comprising:

irradiating different irradiation areas on the object, each area being located on the same surface intersecting with an optical axis of the plurality of measuring beams, with the plurality of measuring beams scanned by a scanning unit; and detecting each of the plurality of combined beams within a different measurable range in a depth direction of the object.

8. The optical tomographic imaging method according to claim 7, wherein the object is an eyeball, wherein the plurality of measuring beams include a first measuring beam and a second measuring beam, wherein a combined beam produced from the first measuring beam is used to acquire a tomographic image of a macula on a fundus portion in the eyeball, and wherein a combined beam produced from the second measuring beam is used to acquire a tomographic image of an optic disc on the fundus portion in the eyeball.

9. The optical tomographic imaging apparatus according to claim 1, wherein the object is an eyeball, wherein the plurality of measuring beams include a first measuring beam, a second measuring beam, and a third measuring beam, wherein a combined beam produced from one of the first measuring beam and the third measuring beam is used to acquire a tomographic image of one of a macula and an optic disc on a fundus portion in the eyeball, and wherein a combined beam produced from the second measuring beam is used to acquire a tomographic image of the other of the macula and the optic disc.

10. The optical tomographic imaging method according to claim 7, wherein the object is an eyeball, wherein the plurality of measuring beams include a first measuring beam, a second measuring beam, and a third measuring beam, wherein a combined beam produced from one of the first measuring beam and the third measuring beam is used to acquire a tomographic image of one of a macula and an optic disc on a fundus portion in the eyeball, and wherein a combined beam produced from the second measuring beam is used to acquire a tomographic image of the other of the macula and the optic disc.

11. The optical tomographic imaging apparatus according to claim 6, wherein the detecting unit includes a first line camera for the macula on the fundus portion in the eyeball and a second line camera for the optic disc on the fundus portion in the eyeball, and wherein a spectral width in the first line camera is larger than a spectral width in the second line camera.

12. A non-transitory computer-readable storage medium storing a program for causing a computer to execute the optical tomographic imaging method according to claim 7.

13. The optical tomographic imaging apparatus according to claim 1, further comprising:

a spectral width changing unit, wherein the object is an eyeball, and the spectral width changing unit is configured to change spectral widths of the combined beams depending on whether the eyeball is the right eye or the left eye.

14. The optical tomographic imaging apparatus according to claim 1, wherein the detecting unit includes a plurality of sensors, and a maximal wavelength and a minimal wavelength of a detected wavelength range of each combined beam are varied among each of the plurality of sensors.

15. The optical tomographic imaging apparatus according to claim 1, wherein each of the different irradiation areas has a different depth, and wherein the optical tomographic imaging apparatus further comprises an acquiring unit configured to acquire tomographic images of different depth ranges based on the detected each of the plurality of combined beams.

16. The optical tomographic imaging apparatus according to claim 15, wherein the object is an eyeball, wherein the detecting unit includes a first line camera for the macula on the fundus portion in the eyeball and a second line camera for the optic disc on the fundus portion in the eyeball, and wherein in the detecting unit, a measurable range in a depth direction in the first line camera is smaller than a measurable range in the depth direction in the second line camera.

17. The optical tomographic imaging method according to claim 7, wherein each of the different irradiation areas has a different depth, and wherein the optical tomographic imaging method further comprises acquiring tomographic images of different depth ranges based on the detected each of the plurality of combined beams.

* * * * *